US00PP13959P29

(12) United States Plant Patent
Alvarado

(10) Patent No.: US PP13,959 P2
(45) Date of Patent: Jul. 8, 2003

(54) DRACAENA PLANT NAMED 'ULISES'

(76) Inventor: Arturo Fernandez Alvarado, PO Box 310-3000, Heredia (CR)

( * ) Notice: Subject to any disclaimer, the term of this patent is extended or adjusted under 35 U.S.C. 154(b) by 0 days.

(21) Appl. No.: 10/047,813

(22) Filed: Jan. 22, 2002

(51) Int. Cl.[7] ..... A01H 5/00
(52) U.S. Cl. ..... Plt./383
(58) Field of Search ..... Plt./383

(56) References Cited

PUBLICATIONS

UPOV–ROM GTITM Computer Database 2002/05, GTI Jouve Software, Citation for 'Ulises'.*

* cited by examiner

*Primary Examiner*—Bruce R. Campell
*Assistant Examiner*—Annette H. Para
(74) *Attorney, Agent, or Firm*—Foley & Lardner

(57) ABSTRACT

A distinct Dracaena plant named 'Ulises' characterized by its relatively compact plant growth; leaves which are of an average length of 30 cm and an average width of 5 cm; distinctive leaf color with a dark green margin closest to RHS 139A; leaf width approximately 0.8 cm, a leaf center which is green RHS 137A to grey-green between RHS 189A and RHS 191A to RHS 191B; stripes approximately 3 cm wide, and between the margin and center of the leaf a white area which is approximately 1 mm wide.

2 Drawing Sheets

BACKGROUND OF THE INVENTION

The present invention comprises a new and distinct cultivar of Dracaena plant botanically known as *Dracaena Vand*. Ex. *L. deremensis* Warneckii and hereinafter referred to by the cultivar name 'Ulises'.

The new cultivar was selected by the inventor, Arturo Fernandez Alvarado, in Heredia, Costa Rica, in 1995. The new cultivar was obtained as a natural mutation (as a sport) of Dracaena Vand. Ex. L. deremensis 'Warneckii'(unpatented).

The new cultivar was first asexually propagated by cuttings by the inventor in Heredia, Costa Rica, in June 1995. Subsequent asexual reproduction of the new cultivar by taking cuttings, has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and in combination distinguish 'Ulises' as a new and distinct cultivar:

1. Variegated with deep green leaves;
2. Tough and tick leaves;
3. Big and concave leaves;
4. Vigorous growth; and
5. Good resistance against stresses and diseases.

'Ulises' has not been observed under all possible environmental conditions. The phenotype on the new cultivar may vary significantly with variations in environment such as temperature, light intensity, and day length without any change in genotype. The following observations, measurements and values describe plants grown in Berkel en Roodenrijs under normal commercial greenhouse conditions which closely approximate those generally used in horticultural practice.

In comparison with the well-known cultivar *Dracaena deremensis* 'Warneckii' (unpatented), 'Ulises' has The leaves of *Dracaena deremensis* Warneckii are realtively much more greyish green and do not have the deep green color that the leaves 'Ulises' have. Compared to *Dracaena deremensis* 'Warneckii', 'Ulises' has much tougher and thicker leaves, which are much less susceptable to transportation, logistic and other damage. When looking at the cross section of the leaves, the shape of the leaves of 'Ulilses' is concave whereas the shape of the leaves of *Dracaena deremensis* 'Warneckii' is not. Compared to 'Warneckii' the leaves of 'Ulises' are somewhat broader and the mid-rib of the leaves of 'Ulises' is much bigger and thicker. 'Ulises' grows faster and more vigorously and is more resistant to adverse conditions such as pests, diseases and climate than *Dracaena deremensis* 'Warneckii'.

BRIEF DESCRIPTION OF THE DRAWING

The accompanying photographs illustrate 10 week old plants grown on a 30 cm (25 weeks old), a 60 cm (50 weeks old) and 120 cm (20 weeks old) long cane, respectively, of Dracaena 'Ulises', with colors being as true as possible with illustrations of this type.

The first drawing shows an image of the 'Ulises' plant on the left and a 'Warneckii' plant of similar age on the right.

The second drawing shows a close up of the same 'Ulises' plant on the left and a leaf comparion of Warneckii (left) and 'Ulises' (right).

DETAILED BOTANICAL DESCRIPTION

Color references are made to The Royal Horticultural Society Colour Chart (R.H.S.), except where general colors of ordinary significance are used. Colors are approximate as color depends on horticultural practices such as light level and fertilization rate, among others.

Classification:

*Botanical.*—*Dracaena Vand.* Ex. *L. deremensis.*

*Commercial.*—*Dracaena deremensis* cv. Ulises.

Parentage: *Dracaena deremensis 'Warneckii'.*

Propagation: Vegetative (cuttings).

General observations:

*Growing conditions.*—In the Netherlands, 'Ulises'is grown in a greenhouse under 20–21 degrees Celsius temperatures day and night. As with most Dracaena varieties, 'Ulises' does not stand direct sunlight (though more than other Dracaena varieties) so sun shields are closed when sunlight becomes too bright. No artificial lighting or photoperiodic treatments are conducted. Highest temperature resistance is at least 40 degrees Celsius, lowest is 5 degrees Celsius. Resistance, tolerance, and susceptibility to stresses, pathogens, and pests is very good. Compound fertilizer is added to the soil. There are no other cultural or environmental treatments.

*Plant vigor.*—Moderate.

Plant habit:

*Growth rate.*—2 cm per weeks.

*Forms.*—Upright.

*Plant height.*—80 cm (grown on a cane of 60 cm).

*Plant width.*—70 cm.

Leaves:

*Form and size.*—Linear-lanceolate, average length: 30 cm, average width: 5 cm (varies from 4.1 cm–5.8 cm), only slightly bent downwards.

*Texture.*—Smooth, glossy, furrowed at main vein.

*Veins.*—Parallel, main vein furrowed.

*Under side color.*—Margins (average 0.8 cm) green, between RHS 147A (yellow-green) and RHS 137A and darker than but closest to RHS 141A (green). Leaves striped vertically, white RHS 155B and greyed-green; RHS 189D to RHS 191A and RHS 191B.

*Upper side color.*—Margins (average 0.8 cm) in between green, RHS 139A and yellow green, RHS 147A. Leaves striped vertically, white, RHS 155C, green, RHS 137A and greyed-green, RHS 189A to RHS 191A and RHS 191B.

*Margin.*—Entire and only slightly wavy.

*Thickness.*—Not very thick, moderately leathery.

*Number.*—Average of 25 leaves per 25 cm stem length.

Flowers: No inflorescences or flowers observed to date. Dracaenas only flower when the growing conditions are very poor (survival instinct of the plant).

Stem:

*Length.*—Cane is 60 cm, plant is 40 cm.

*Diameter.*—1.5 cm (on young shoots), older shoots grow thicker when aging.

*Color.*—Green, darker than but closest to RHS 139A with yellow-green, RHS 145C to 145D and greyed-green, RHS 192B to RHS 192C markings.

Roots: Moderately branching, greyed-orange in color, RHS 164B to RHS 164C. Time to initiate root development: 3 weeks after cutting.

Plant disease/insect tolerance: Less susceptible to pests and diseases than similar varieties because of its tougher and thicker leaves.

Reproductive organs: No reproductive organs observed to date.

I claim:

1. A new and distinct cultivar of Dracaena plant named 'Ulises', as described and illustrated herein.

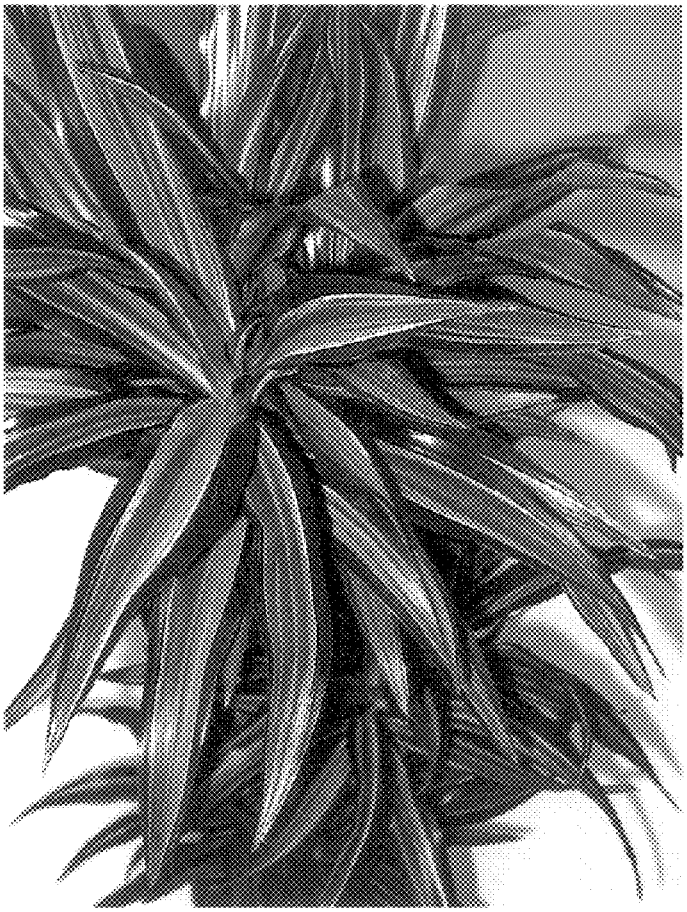
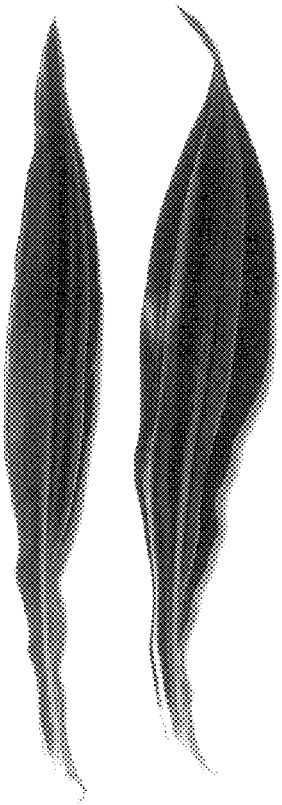

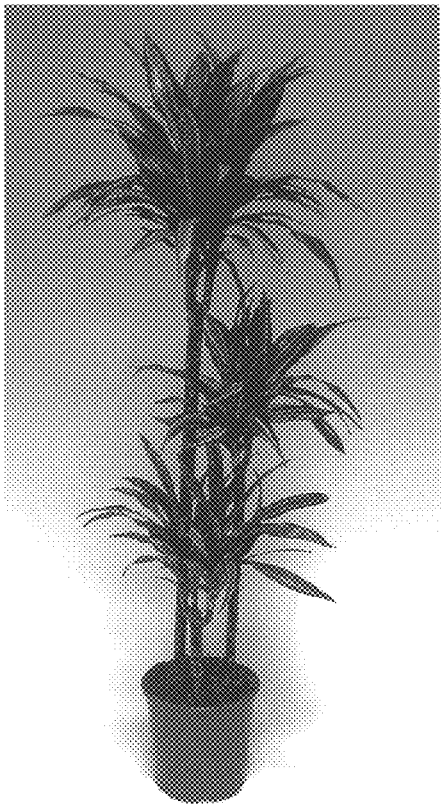
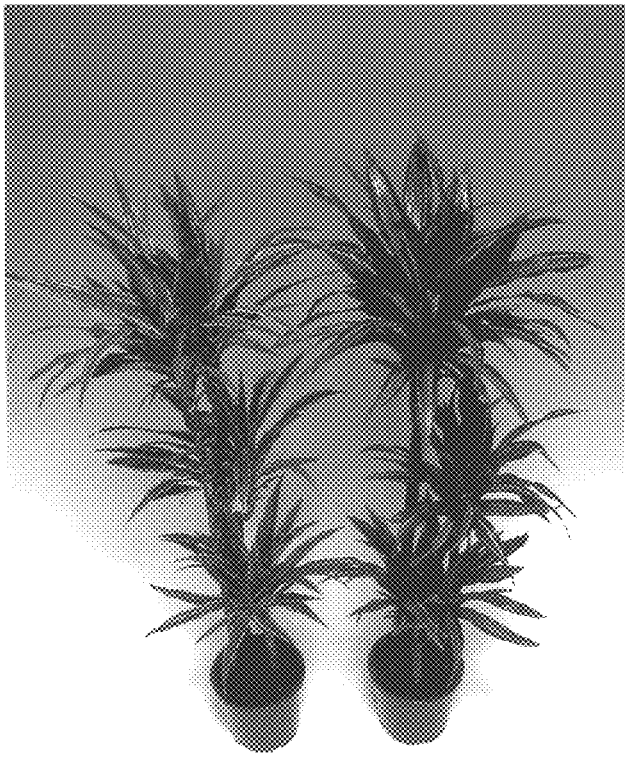

* * * * *